United States Patent
Wei et al.

(10) Patent No.: US 11,592,439 B2
(45) Date of Patent: Feb. 28, 2023

(54) PRETREATMENT AGENT IN NON-AGGLUTINATION ASSAYS

(71) Applicant: Siemens Healthcare Diagnostics Inc., Tarrytown, NY (US)

(72) Inventors: Tie Q. Wei, Wilmington, DE (US); Christy Schaible, Oxford, PA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 337 days.

(21) Appl. No.: 16/824,136

(22) Filed: Mar. 19, 2020

(65) Prior Publication Data

US 2020/0217839 A1 Jul. 9, 2020

Related U.S. Application Data

(63) Continuation of application No. 16/225,469, filed on Dec. 19, 2018, now abandoned, which is a continuation of application No. 15/103,534, filed as application No. PCT/US2014/069520 on Dec. 10, 2014, now abandoned.

(60) Provisional application No. 61/915,755, filed on Dec. 13, 2013.

(51) Int. Cl.
  *G01N 33/53* (2006.01)
  *G01N 33/94* (2006.01)

(52) U.S. Cl.
  CPC ..... *G01N 33/5306* (2013.01); *G01N 33/9493* (2013.01)

(58) Field of Classification Search
  CPC .................. G01N 33/5306; G01N 33/9493
  See application file for complete search history.

(56) References Cited

U.S. PATENT DOCUMENTS

| | | | |
|---|---|---|---|
| 4,121,975 A | 10/1978 | Ullman et al. | |
| 4,362,531 A | 12/1982 | de Steenwinkel et al. | |
| 4,536,478 A | 8/1985 | Sokoloff et al. | |
| 5,691,150 A | 11/1997 | Mori et al. | |
| 6,187,547 B1 * | 2/2001 | Legay | G01N 33/9493 435/7.1 |
| 7,186,518 B2 | 3/2007 | Wang et al. | |
| 2005/0208607 A1 * | 9/2005 | Roberts | G01N 33/9493 435/7.92 |
| 2008/0227118 A1 | 9/2008 | Kohno et al. | |
| 2009/0311724 A1 | 12/2009 | Levison et al. | |
| 2009/0317922 A1 * | 12/2009 | Levison | G01N 33/5306 436/517 |
| 2011/0129815 A1 | 6/2011 | Yamagaito et al. | |

FOREIGN PATENT DOCUMENTS

| | | |
|---|---|---|
| CN | 101769920 A | 7/2010 |
| EP | 0218309 A2 | 4/1987 |
| JP | H07311200 | 11/1995 |
| JP | 2002503812 A | 2/2002 |
| JP | 2009288149 A | 12/2009 |
| WO | 9803877 A1 | 1/1998 |
| WO | 2007111847 A2 | 10/2007 |
| WO | 2009020468 A2 | 2/2009 |

OTHER PUBLICATIONS

International Search Report and Written Opinion of International Application No. PCT/US2014/069520 dated Mar. 13, 2015.
European Search Report and Written Opinion of European Application No. EP 14870173.3 dated Dec. 6, 2016.
European Decision to Grant of European Application No. EP 14870173.3 dated Nov. 26, 2018.

* cited by examiner

Primary Examiner — Shafiqul Haq

(57) ABSTRACT

Methods and reagents are disclosed for minimizing a false result in an assay measurement for determining a concentration of an analyte in a sample suspected of containing the analyte. The method comprises pretreating both an antibody and a sample to be subjected to a non-agglutination immunoassay. In the method the antibody and the sample are combined with a pretreatment agent selected from the group consisting of hydroxyphenyl-substituted C1-C5 carboxylic acids and metallic salts thereof and halogen-substituted C1-C5 carboxylic acids and metallic salts thereof in an amount effective to enhance the accuracy of the non-agglutination immunoassay.

16 Claims, No Drawings

PRETREATMENT AGENT IN NON-AGGLUTINATION ASSAYS

CROSS REFERENCE TO RELATED APPLICATIONS/INCORPORATION BY REFERENCE STATEMENT

This application is a continuation of U.S. Ser. No. 16/225,469, filed Dec. 19, 2018, now abandoned; which is a continuation of U.S. Ser. No. 15/103,534, filed Jun. 10, 2016, now abandoned; which claims the benefit as a US National Stage application under 35 USC § 371 of International Application No. PCT/US2014/069520, filed Dec. 10, 2014; which claims priority under 35 USC § 119(e) of U.S. Provisional Application No. 61/915,755, filed Dec. 13, 2013. The entirety of the above-referenced patents and patent applications are hereby expressly incorporated herein by reference.

BACKGROUND

The present disclosure relates to methods and kits for determining the concentration of an analyte in a sample suspected of containing the analyte. More particularly, the present disclosure relates to reducing false results in the measurements conducted during the above methods for determining the concentration of an analyte in a sample.

The body relies upon a complex immune response system to distinguish self from non-self. At times, the body's immune system must be controlled in order to either augment a deficient response or suppress an excessive response. For example, when organs such as kidney, heart, heart-lung, bone marrow and liver are transplanted in humans, the body will often reject the transplanted tissue by a process referred to as allograft rejection.

In treating allograft rejection, the immune system is frequently suppressed in a controlled manner with drug therapy. Immunosuppressant drugs are carefully administered to transplant recipients in order to help prevent allograft rejection of non-self tissue. Two most commonly administered immunosuppressive drugs to prevent organ rejection in transplant patients are Cyclosporine (CSA) and FK-506 (FK or tacrolimus). Another drug that finds use as an immunosuppressant in the United States and other countries is sirolimus, also known as rapamycin. Derivatives of sirolimus are also said to be useful as immunosuppressants. Such derivatives include, for example, Everolimus.

The side effects associated with some immunosuppressant drugs can be controlled in part by carefully controlling the level of the drug present in a patient. Therapeutic monitoring of concentrations of immunosuppressant drugs and related drugs in blood is required to optimize dosing regimes to ensure maximal immunosuppression with minimal toxicity. Although immunosuppressant drugs are highly effective immunosuppressive agents, their use must be carefully managed because the effective dose range is often narrow and excessive dosage can result in serious side effects. On the other hand, too little dosage of an immunosuppressant can lead to tissue rejection. Because the distribution and metabolism of an immunosuppressant drug can vary greatly between patients and because of the wide range and severity of adverse reactions, accurate monitoring of the drug level is essential.

In the therapeutic drug monitoring field, selectively detecting a drug over other substances in a sample suspected of containing the drug is often an important goal for designing immunoassays. This is especially true for immunosuppressant drugs. For that reason, HPLC tandem MS assays have become standard methods for the measurement of sirolimus, tacrolimus and other immunosuppressant drugs due to their ability to selectively measure the parent drug. However, the above methods are costly and time-consuming and are often employed to verify positive results obtained by another assay method first rather than being used in laboratories as an initial determination.

Most whole blood assays for immunosuppressant drugs require a manual step using reagents to extract the drug from blood constituents. As a result, the drug molecules and drug metabolite molecules are dissociated from endogenous binding proteins and are extracted into a relatively clean solution in which plasma proteins and lipoprotein particles as well as most other molecules are removed. Because precipitation techniques are usually used, the extracted sample is basically free of most blood macromolecules including drug-binding proteins. Thus, in the extracted samples, the parent drug and its metabolites are dissolved as unbound, individual molecules and compete with one another for reaction with an assay antibody in the immunoreaction mixture. The binding of the assay antibody to the drug occurs in the absence of most endogenous substances in these assays. The cross-reactivity of a drug metabolite depends mostly on its antibody binding affinity in such assays.

In a homogeneous assay for an immunosuppressant drug where there is no manual extraction or separation of the drug from blood constituents, an antibody for the immunosuppressant drug has to detect the drug in the presence of most or all blood constituents. The presence of these constituents might interfere with the binding of the antibody to the immunosuppressant drug and lead to a false assay result.

There is, therefore, a continuing need to develop fast and accurate diagnostic methods to measure levels of analytes in samples taken from a patient. The methods should be fully automatable and be accurate even when conducted on samples having various interfering substances present. The assay should provide an accurate measurement of the amount of the analyte in the sample, while minimizing inaccuracies resulting from interfering substances present in the sample. Reduction in false assay measurements is important to the accuracy of the methods.

DETAILED DESCRIPTION

General Discussion

The present disclosure is directed to the accurate measurement of analyte concentration in a sample by reducing or eliminating false assay results in a non-agglutination immunoassay. In examples of methods in accordance with the principles described herein, an antibody and a sample to be subjected to a non-agglutination immunoassay are combined with a pretreatment agent selected from the group consisting of hydroxyphenyl-substituted C1-C5 carboxylic acids and metallic salts thereof and halogen-substituted C1-C5 carboxylic acids and metallic salts thereof, or a combination of two or more of the above, in an amount effective to enhance the accuracy of the non-agglutination immunoassay.

One example in accordance with the principles described herein is directed to a method of pretreating both an antibody and a sample to be subjected to a non-agglutination immunoassay. In the method the antibody and the sample are combined with a pretreatment agent selected from the group consisting of hydroxyphenyl-substituted C1-C5 carboxylic acids and metallic salts thereof and halogen-substituted C1-C5 carboxylic acids and metallic salts thereof in an amount effective to enhance the accuracy of the non-agglutination immunoassay.

Another example in accordance with the principles described herein is directed to a method of determining an analyte in a sample suspected of containing the analyte. The method comprises a non-agglutination immunoassay. In the non-agglutination immunoassay, a combination is provided in a medium where the combination comprises the sample, an antibody reagent comprising an antibody for the analyte, and a pretreatment agent selected from the group consisting of hydroxyphenyl-substituted C1-C5 carboxylic acids and metallic salts thereof and halogen-substituted C1-C5 carboxylic acids and metallic salts thereof in an amount effective to enhance the accuracy of the non-agglutination immunoassay. The medium is incubated under conditions for binding of the antibody for the analyte to analyte suspected of being in the sample. The medium is examined for the presence of a complex comprising the analyte and the antibody for the analyte, the presence and/or amount of the complex indicating the presence and/or amount of the analyte in the sample.

Another example in accordance with the principles described herein is directed to a method of determining an immunosuppressant drug in a sample suspected of containing the immunosuppressant drug. The method comprising a non-agglutination immunoassay. In the method a combination is provided in a medium. The combination comprises the sample, a releasing agent for releasing the immunosuppressant drug from endogenous binding substances, an antibody reagent comprising an antibody for the immunosuppressant drug, and a pretreatment agent selected from the group consisting of hydroxyphenyl-substituted C1-C5 carboxylic acids and metallic salts thereof and halogen-substituted C1-C5 carboxylic acids and metallic salts thereof in an amount effective to enhance the accuracy of the non-agglutination immunoassay. The medium is incubated under conditions for binding of the antibody for the immunosuppressant drug to the immunosuppressant drug suspected of being in the sample. The medium is examined for the presence of a complex comprising the immunosuppressant drug and the antibody for the immunosuppressant drug, the presence and/or amount of the complex indicating the presence and/or amount of the immunosuppressant drug in the sample.

An "antibody" is a member of a specific binding pair ("sbp member"), which is one of two different molecules, having an area on the surface or in a cavity, which specifically binds to and is thereby defined as complementary with a particular spatial and polar organization of the other molecule. The members of the specific binding pair will usually be members of an immunological pair such as antigen-antibody, although other specific binding pairs such as, for example, biotin-avidin, hormones-hormone receptors, enzyme-substrate, nucleic acid duplexes, IgG-protein A, and polynucleotide pairs such as DNA-DNA, DNA-RNA, are not immunological pairs but are included within the scope of sbp member. Accordingly, specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules.

A "non-agglutination" immunoassay is an assay employing at least one antibody or similar macromolecular member of a specific binding pair where the assay does not involve the aggregation of substances such as particulate materials, for example, bacteria, cells, or latex particles, by virtue of the binding of antigens on the substances to the antibody or similar macromolecular sbp member.

C1-C5 carboxylic acids refers to carboxylic acids having from 1 to 5 carbon atoms, or 1 to 4 carbon atoms, or 1 to 3 carbon atoms, or 1 to 2 carbon atoms, or 2 to 5 carbon atoms, or 2 to 4 carbon atoms, or 2 to 3 carbon atoms, or 3 to 5 carbon atoms, or 4 to 5 carbon atoms. Examples of C1-C5 carboxylic acids include, by way of illustration and not limitation, formic acid, acetic acid, propionic acid, n-butanoic acid, iso-butanoic acid, n-pentanoic acid, iso-pentanoic acid, for example.

In some examples, the C1-C5 carboxylic acid is substituted with a hydroxyphenyl substituent, which is a phenyl group comprising at least one hydroxy group, or at least two hydroxy groups. The hydroxy substituent may be ortho (o), meta (m) or para (p) to the carbon atom of the phenyl ring that is attached to the C1-C5 carboxylic acid. Examples of hydroxyphenyl C1-C5 carboxylic acids include, but are not limited to, (o-hydroxyphenyl)formic acid (salicylic acid), (m-hydroxyphenyl)formic acid, (p-hydroxyphenyl)formic acid, (o-hydroxyphenyl)acetic acid, (m-hydroxyphenyl)acetic acid, and (p-hydroxyphenyl)acetic acid, for example.

In some examples, the hydroxyphenyl-substituted C1-C5 carboxylic acids are in the form of a metal salt. The metal of the metal salt may be, by way of illustration and not limitation, a metal of Group 1 of the periodic table, or a metal of Group 2 of the periodic table, for example. In some examples, the metal of the metallic salt of hydroxyphenyl-substituted C1-C5 carboxylic acid is, but is not limited to, sodium, potassium, or lithium, for example. In a particular example in accordance with the principles described herein, the metallic salt of hydroxyphenyl-substituted C1-C5 carboxylic acid is sodium salicylate.

Halogen-substituted C1-C5 carboxylic acids are those C1-C5 carboxylic acids that comprise at least one halogen substituent, or at least two halogen substituents, or at least 3 halogen substituents. In some examples, the number of halogen substituents may be in the range of, for example, 1-4, or 1-3, or 1-2, or 2-4, or 3-4, or 2-3. In some examples, the number of halogen substituents may be 1, or 2, or 3, or 4, for example. The halogen substituent may be, for example, one or more of chlorine, bromine, fluorine and iodine. In some examples in accordance with the principles described herein, the halogen-substituted C1-C5 carboxylic acid may be, but is not limited to, chloroacetic acid, dichloroacetic acid, trichloroacetic acid, 2-chloropropionic acid, 2,2-dichloropropionic acid, 2,2,2-trichloropropionic acid, 2,3-dichloropropionic acid, 2,3,3-trichloropropionic acid, bromoacetic acid, dibromoacetic acid, tribromoacetic acid, 2-bromopropionic acid, 2,2-dibromopropionic acid, 2,2,2-tribromopropionic acid, 2,3-dibromopropionic acid, 2,3,3-tribromopropionic acid, iodoacetic acid, diiodoacetic acid, triiodoacetic acid, 2-iodopropionic acid, 2,2-diiodopropionic acid, 2,2,2-triiodopropionic acid, 2,3-diiodopropionic acid, and 2,3,3-triiodopropionic acid, for example. In some examples, the halogen-substituted C1-C5 carboxylic acid may be in the form of a metallic salt where the metal of the metallic salt is from Group 1 or Group 2 of the periodic table as discussed above for the metallic salt of the hydroxyphenyl-substituted C1-C5 carboxylic acids. In a particular example in accordance with the principles described herein, the metallic salt of halogen-substituted C1-C5 carboxylic acid is sodium trichloroacetate.

In examples of methods in accordance with the principles described herein, an antibody and a sample to be subjected to a non-agglutination immunoassay are combined with a pretreatment agent as discussed above in an aqueous medium, which may be an aqueous buffered medium. The medium may be a medium in which a non-agglutination immunoassay is conducted in accordance with the principles described herein or a medium employed for conducting the pretreatment method. The pH for the aqueous medium will usually be in the range of about 4 to about 11, or in the range of about 5 to about 10, or in the range of about 6.5 to about 9.5.

Various buffers may be used to achieve the desired pH and maintain the pH during the procedure. Illustrative buffers include borate, phosphate, carbonate, tris, barbital and the like. The particular buffer employed is not critical, but in an individual assay one or another buffer may be preferred. Various ancillary materials may be employed in the above methods. For example, in addition to buffers the medium may comprise stabilizers for the medium and for the reagents employed. In some embodiments, in addition to these additives, proteins may be included, such as albumins; quaternary ammonium salts; polyanions such as dextran sulfate; and binding enhancers, for example. All of the above materials are present in a concentration or amount sufficient to achieve the desired effect or function.

The pretreatment agent is employed in an amount sufficient to enhance the accuracy of the non-agglutination assay. The amount of the pretreatment agent is dependent on one or more of the nature of the non-agglutination assay, the nature of the antibody reagent, the amount of the sample, the suspected range of the amount of an analyte in a sample, the amount of other substances suspected of being in the sample, and the presence of metabolites and/or phospholipids, for example. In some examples, the amount or concentration (weight percent) of the pretreatment agent in the assay medium is about 1% to about 75%, or about 1% to about 50%, or about 1% to about 40%, or about 1% to about 30%, or about 1% to about 20%, or about 1% to about 10%, or about 1% to about 5%, or about 5% to about 75%, or about 5% to about 50%, or about 5% to about 40%, or about 5% to about 30%, or about 5% to about 20%, or about 5% to about 10%, or about 10% to about 75%, or about 10% to about 50%, or about 10% to about 40%, or about 10% to about 30%, or about 10% to about 20%, or about 10% to about 15%, for example.

The sample to be tested may be non-biological or biological. "Non-biological samples" are those that do not relate to a biological material and include, for example, soil samples, water samples, air samples, samples of other gases and mineral samples. The phrase "biological sample" refers to any biological material such as, for example, body fluid, body tissue, body compounds and culture media. The sample may be a solid, semi-solid or a fluid (a liquid or a gas) from any source. In some embodiments the sample may be a body excretion, a body aspirant, a body excisant or a body extractant. The body is usually that of a mammal and in some embodiments the body is a human body. Body excretions are those substances that are excreted from a body (although they also may be obtained by excision or extraction) such as, for example, urine, feces, stool, vaginal mucus, semen, tears, breath, sweat, blister fluid and inflammatory exudates. Body excisants are those materials that are excised from a body such as, for example, skin, hair and tissue samples including biopsies from organs and other body parts. Body aspirants are those materials that are aspirated from a body such as, for example, mucus, saliva and sputum. Body extractants are those materials that are extracted from a body such as, for example, whole blood, plasma, serum, spinal fluid, cerebral spinal fluid, lymphatic fluid, synovial fluid and peritoneal fluid.

The amount of the sample subjected to an assay is dependent on one or more of the nature of the analyte, the nature of the assay, the nature of the various reagents for conducting the assay, and the nature of the complex comprising the analyte, for example. In some examples, the volume of the sample is about 1 µL to about 100 µL, or about 2 µL to about 100 µL, or about 5 µL to about 100 µL, or about 104 to about 100 µL, or about 1 µL to about 80 µL, or about 1 µL to about 60 µL, or about 1 µL to about 40 µL, or about 1 µL to about 20 µL, or about 5 µL to about 50 µL, or about 104 to about 50 µL, for example.

The analyte is a substance of interest or the compound or composition to be detected and/or quantitated. Analytes include, by way of illustration and not limitation, therapeutic drugs, drugs of abuse, metabolites, pesticides, volatile organic compounds, semi-volatile organic compounds, non-volatile organic compounds, proteins, polysaccharides, pollutants, toxins, lipids and nucleic acids, (DNA, RNA), for example.

Representative drug analytes, by way of illustration and not limitation, include alkaloids, steroids, lactams, amino-alkylbenzenes, benzheterocyclics, purines, drugs derived from marijuana, hormones, polypeptides which includes proteins, immunosuppressants, vitamins, prostaglandins, tricyclic antidepressants, anti-neoplastics, nucleosides and nucleotides including polynucleosides and polynucleotides, miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, and metabolites and derivatives of all of the above.

Also included within the term analyte are metabolites related to disease states, aminoglycosides, such as gentamicin, kanamicin, tobramycin, and amikacin, and pesticides such as, for example, polyhalogenated biphenyls, phosphate esters, thiophosphates, carbamates and polyhalogenated sulfenamides and their metabolites and derivatives.

The term analyte also includes combinations of two or more of polypeptides and proteins, polysaccharides and nucleic acids. Such combinations include, for example, components of bacteria, viruses, chromosomes, genes, mitochondria, nuclei and cell membranes. Protein analytes include, for example, immunoglobulins, cytokines, enzymes, hormones, cancer antigens, nutritional markers and tissue specific antigens. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase, myoglobin, CPK-MB and calcitonin, and peptide hormones. Other polymeric materials of interest are mucopolysaccharides and polysaccharides. As indicated above, the term analyte further includes oligonucleotide and polynucleotide analytes such as m-RNA, r-RNA, t-RNA, DNA and DNA-RNA duplexes, for example.

In some examples in accordance with the principles described herein, the analyte is an immunosuppressant drug, which is a therapeutic drug that is administered to transplant recipients in order to help prevent allograft rejection of non-self tissue. Immunosuppressant drugs can be classified as follows: glucocorticoids, cytostatics, antibodies, drugs acting on immunophilins and other drugs such as interferons, opiates INF binding proteins, mycophenolate, and FTY720, for example. A particular class of immunosuppressant drugs comprises those drugs that act on immunophilins. Immunophilins are an example of high-affinity, specific binding proteins having physiological significance. Two distinct families of immunophilins are presently known: cyclophilins and macrophilins, the latter of which specifically bind, for example, tacrolimus or sirolimus. The immunosuppressant drugs that act on immunophilin include, for example, cyclosporin (including cyclosporin A, cyclosporin B, cyclosporin C, cyclosporin D, cyclosporin E, cyclosporin F, cyclosporin G, cyclosporin H, cyclosporin I), tacrolimus (FK506, PROGRAFI, sirolimus (rapamycin, RAPAMUNE®, and everolimus (RAD, CERTICAN®).

Some examples in accordance with the principles described herein are directed to non-agglutination assay methods of determining an analyte in a sample suspected of containing the analyte. In the non-agglutination assay, a combination is provided in a medium where the combination comprises the sample, an antibody reagent comprising an antibody for the analyte, and an agent selected from the group consisting of metallic salts of hydroxyphenyl-substituted C1-C5 carboxylic acids and halogen-substituted C1-C5 carboxylic acids in an amount effective to enhance the accuracy of the non-agglutination assay.

The antibody reagent comprises an antibody for the analyte, that is, an antibody that specifically binds to the analyte. The antibody reagent may further comprise one or more labels or labeled reagent. The antibody reagent includes those agents necessary for the detection of the analyte. The label is usually part of a signal producing system ("sps"). The nature of the label is dependent on the particular non-agglutination assay format. An sps usually includes one or more components, at least one component being a detectable label, which generates a detectable signal that relates to the amount of bound and/or unbound label, i.e. the amount of label bound or not bound to the analyte being detected or to an agent that reflects the amount of the analyte to be detected. The label is any molecule that produces or can be induced to produce a signal, and may be, for example, a fluorescer, radiolabel, enzyme, chemiluminescer or photosensitizer. Thus, the signal is detected and/or measured by detecting enzyme activity, luminescence, light absorbance or radioactivity, and so forth, as the case may be.

Suitable labels include, by way of illustration and not limitation, enzymes such as β-galactosidase, alkaline phosphatase, glucose-6-phosphate dehydrogenase ("G6PDH") and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; complexes such as those prepared from CdSe and ZnS present in semiconductor nanocrystals known as Quantum dots; chemiluminescers such as isoluminol and acridinium esters, for example; sensitizers; coenzymes; enzyme substrates; radiolabels such as $^{125}I$, $^{131}I$, $^{14}C$, $^{3}H$, $^{57}Co$ and $^{75}Se$; particles such as latex particles, carbon particles, metal particles including magnetic particles, e.g., chromium dioxide ($CrO_2$) particles, and the like; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescers and chemiluminescers are disclosed in Litman, et al., U.S. Pat. No. 4,275,149, at columns 30 and 31; which are incorporated herein by reference.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal. Such other components may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al., U.S. Pat. No. 5,185,243, columns 11-13, incorporated herein by reference.

The label or other sps members can be bound to a support. An analyte derivative or analyte analog may be bound to a solid support in any manner known in the art, provided only that the binding does not substantially interfere with the analogs ability to bind with an antibody. In some embodiments, the analyte derivative or analyte analog may be coated or covalently bound directly to the solid phase or may have layers of one or more carrier molecules such as poly(amino acids) including proteins such as serum albumins or immunoglobulins, or polysaccharides (carbohydrates) such as, for example, dextran or dextran derivatives. Linking groups may also be used to covalently couple the solid support and the analyte analog. Other methods of binding the analyte derivatives are also possible. For instance, a solid support may have a coating of a binder for a small molecule such as, for example, avidin or an antibody, and a small molecule such as, e.g., biotin or hapten, can be bound to the analyte derivative or vice versa. The binding of components to the surface of a support may be direct or indirect, covalent or non-covalent and can be accomplished by well-known techniques, commonly available in the literature. See, for example, "Immobilized Enzymes," Ichiro Chibata, Halsted Press, New York (1978) and Cautrecasas, *J. Biol. Chem.,* 245:3059 (1970).

The support may be comprised of an organic or inorganic, solid or fluid, water insoluble material, which may be transparent or partially transparent. The support can have any of a number of shapes, such as particle, including bead, film, membrane, tube, well, strip, rod, planar surfaces such as, e.g., plate, paper, etc., or fiber. Depending on the type of assay, the support may or may not be suspendable in the medium in which it is employed. Examples of suspendable supports are polymeric materials such as, but not limited to, latex, lipid bilayers or liposomes, oil droplets, cells and hydrogels, and magnetic particles, for example. Other support compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly(ethylene terephthalate), nylon, and poly(vinyl butyrate), for example, which can be either used by themselves or in conjunction with other materials.

The support may be a particle. The particles should have an average diameter of at least about 0.02 microns and not more than about 100 microns. In some embodiments, the particles have an average diameter from about 0.05 microns to about 20 microns, or from about 0.3 microns to about 10 microns. The particle may be organic or inorganic, swellable or non-swellable, porous or non-porous, preferably (but not by way of limitation) of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus*, or *E. coli*, viruses, for example. The particles can also be particles comprised of organic and inorganic polymers, liposomes, latex particles, magnetic or non-magnetic particles, phospholipid vesicles, chylomicrons, or lipoproteins, for example. In some examples, the particles are chromium dioxide (chrome) particles or latex particles.

The polymer particles can be formed of addition or condensation polymers. The particles will be readily dispersible in an aqueous medium and can be adsorptive or functionalizable so as to permit conjugation to an analyte analog, either directly or indirectly through a linking group. The particles can also be derived from naturally occurring materials, naturally occurring materials that are synthetically modified, and synthetic materials. Among organic polymers of particular interest are polysaccharides, particularly cross-linked polysaccharides, such a agarose, which is available as SEPHAROSE®, dextran, available as SEPHADEX® and SEPHACRYL®, cellulose, and starch, for example; addition polymers, such as polystyrene, polyvinyl alcohol, homopolymers and copolymers of derivatives of acrylate and methacrylate, particularly esters and amides having free hydroxyl functionalities, for example.

The label and/or other sps member may be bound to an sbp member or another molecule. For example, the label can be bound covalently to an sbp member such as, for example, an antibody, a receptor for an antibody, a receptor that is capable of binding to a small molecule conjugated to an antibody, or a ligand (analyte) analog. Bonding of the label to the sbp member may be accomplished by chemical reactions that result in replacing a hydrogen atom of the label with a bond to the sbp member or may include a linking group between the label and the sbp member. Other sps members may also be bound covalently to sbp members. For example, two sps members such as a fluorescer and quencher can each be bound to a different antibody where the antibodies form a specific complex with the analyte. Formation of the complex brings the fluorescer and quencher in close proximity, thus permitting the quencher to interact with the fluorescer to produce a signal. Methods of conjugation are well known in the art. See, for example, Rubenstein, et al., U.S. Pat. No. 3,817,837, incorporated herein by reference.

Enzymes of particular interest as label proteins are redox enzymes, particularly dehydrogenases such as glucose-6-phosphate dehydrogenase and lactate dehydrogenase, for example, and enzymes that involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme that employs the hydrogen peroxide to oxidize a dye precursor, that is, a peroxidase such as horse radish peroxidase, lactoperoxidase, or microperoxidase. Additional enzyme combinations are known in the art. When a single enzyme is used as a label, other enzymes may find use such as hydrolases, transferases, and oxidoreductases, preferably (but not by way of limitation) hydrolases such as alkaline phosphatase and β-galactosidase. Alternatively, luciferases may be used such as firefly luciferase and bacterial luciferase.

Illustrative co-enzymes that find use include NAD[H], NADP[H], pyridoxal phosphate, FAD[H], FMN[H], for example, usually coenzymes involving cycling reactions. See, for example, U.S. Pat. No. 4,318,980, the disclosure of which is incorporated herein by reference.

With label proteins such as, for example, enzymes, the weight average molecular weight range will be from about 10,000 to about 600,000, or from about 10,000 to about 300,000 molecular weight. There is usually at least about 1 analyte analog per about 200,000 molecular weight, or at least about 1 per about 150,000 molecular weight, or at least about 1 per about 100,000 molecular weight, or at least about 1 per about 50,000 molecular weight, for example. In the case of enzymes, the number of analyte analog groups is from 1 to about 20, about 2 to about 15, about 3 to about 12, or about 6 to about 10, for example.

The term "non-poly(amino acid) labels" includes those labels that are not proteins (e.g., enzymes). The non-poly (amino acid) label is capable of being detected directly or is detectable through a specific binding reaction that produces a detectable signal. The non-poly(amino acid) labels include, for example, radioisotopes, luminescent compounds, supports, e.g., particles, plates, beads, etc., polynucleotides, and the like. More particularly, the non-poly (amino acid) label can be isotopic or non-isotopic, usually non-isotopic, and can be a polynucleotide coding for a catalyst, promoter, dye, coenzyme, enzyme substrate, radioactive group, a small organic molecule (including, e.g., biotin, fluorescent molecules, chemiluminescent molecules, and the like), amplifiable polynucleotide sequence, a support such as, for example, a particle such as latex or carbon particle or chromium dioxide (chrome) particle, metal sol, crystallite, liposome, cell, which may or may not be further labeled with a dye, catalyst or other detectable group, for example.

In some examples in accordance with the principles described herein such as, for example, an immunosuppressant drug analyte, a releasing agent may be employed either prior to combining the sample with the antibody reagent or in the combination of the antibody reagent, the sample and the pretreatment agent.

The releasing agent displaces the analyte from endogenous binding moieties. In some embodiments the releasing agent has high binding affinity to the endogenous binding proteins so that it readily displaces the analyte, and its metabolites in some instances, from endogenous binding proteins. In addition, the releasing agent does not bind to any significant degree to an antibody for the analyte that is used in the assay. By the phrase "does not bind to any significant degree" is meant that the extent of binding should be low enough so that an accurate assay for the analyte may be carried out. The releasing agent may be any moiety, either a single compound or a mixture of compounds, which accomplishes the desired result of displacement with no significant binding to an assay antibody.

In some examples the releasing agent is an analog, including structural analogs, of the analyte. A releasing agent that is an analyte analog is a modified drug that can displace the analogous analyte from a binding protein but does not compete to any substantial degree for a receptor such as an antibody for the analyte. The modification provides means to join an analyte analog to another molecule. The analyte analog will usually differ from the analyte by more than replacement of a hydrogen with a bond which links the analyte analog to a hub or label, but need not. The analyte analog may be, for example, the analyte conjugated to another molecule through a linking group, for example. For analytes that comprise a hydroxy or carboxylic acid functionality, the releasing agent may be an ester of the analyte, which has a high binding affinity for endogenous binding proteins relative to the analyte to be detected and which has no significant binding affinity for an antibody for the analyte. For example, in a determination for sirolimus, an ester of sirolimus may be employed as the releasing agent so long as it meets the above requirements. It should be noted that a non-releasing agent analyte analog is a modified analyte that does compete with the corresponding analyte for binding to an antibody for the analyte.

A structural analog is a moiety that has the same or similar structural or spatial characteristics as the analyte such that the structural analog accomplishes the same or similar result as the analog of the analyte. The structural analog may be, for example, another compound that is related to the analyte. For example, as mentioned above, in a determination of sirolimus, an ester of tacrolimus may be employed as a releasing agent, or in a determination of tacrolimus, sirolimus may be employed as a releasing agent. The ester may be, for example, a carbamate, a carbonate, or an ester of a $C_1$ to $C_6$ carboxylic acid, for example. See, for example, U.S. Pat. No. 7,186,518, the relevant disclosure of which is incorporated herein by reference. Other examples of releasing agents include [$Thr_2$, $Leu_5$, D-$Hiv_8$, $Leu_{10}$]-cyclosporin A for cyclosporin A, FK506 for sirolimus, and sirolimus for FK506, for example. See, for example, U.S. Pat. No. 6,187,547, the relevant disclosure of which is incorporated herein by reference.

In some embodiments the releasing agent may be an agent that disrupts cellular membranes in which the analyte is entrapped. For example, an analyte that is entrapped within red blood cells may be released from the red blood cells by employing a hemolytic agent. A hemolytic agent is a compound or mixture of compounds that disrupts the integrity of the membranes of red blood cells thereby releasing intracellular contents of the cells and, in particular, erythrocytes. Numerous hemolytic agents are known in the art. Hemolytic agents include, for example, non-ionic detergents, anionic detergents, amphoteric detergents, low ionic strength aqueous solutions (hypotonic solutions), bacterial agents, antibodies that cause complement dependent lysis, and the like. Non-ionic detergents that may be employed as the hemolytic agent include both synthetic detergents and natural detergents. Examples of synthetic detergents include TRITON™ X-100, TRITON™ N-101, TRITON™ X-114, TRITON™ X-405, TRITON™ SP-135, TWEEN® 20 (polyoxyethylene (20) sorbitan monolaurate), TWEEN® 80 (polyoxyethylene (20) sorbitan monooleate), DOWFAX®, ZONYL®, pentaerythrityl palmitate, ADOGEN® 464, ALKANOL® 6112 surfactant, allyl alcohol 1,2-butoxylate-block-ethoxylate HLB 6, BRIJ®, ethylenediamine tetrakis(ethoxylate-block-propoxylate) tetrol, IGEPAL®, MERPOL®, poly(ethylene glycol), 2-[ethyl[(heptadecafluorooctyl)sulfonyl]amino] ethyl ether, polyethylene-block-poly(ethylene glycol), polyoxyethylene sorbitan tetraoleate, polyoxyethylene sorbitol hexaoleate, TERGITOL® NP-9, GAFAC® (RHODAFAC®, an alkyl polyoxyethylene glycol phosphate ester such as, for example, alpha-dodecyl-omega-hydroxypoly (oxy-1,2-ethanediyl) phosphate), and EP110® and the like. Naturally-occurring detergents that may be employed as the hemolytic agent include, for example, saponins, sodium or potassium neutralized fatty acid, neutralized phospholipids, diacylglycerol, neutralized phosphatidyl serine, phosphatidate, neutralized phosphatidyl ethanolamine, phosphatidyl choline, phosphatidyl inositol, phosphatidylcholine, bile salt, unesterified cholesterol, neutralized sphingosine, ceramide, and the like. Combinations of one or more synthetic detergents or one or more naturally occurring detergents and combinations of synthetic detergents and naturally occurring detergents may also be employed.

Other releasing agents that may be employed in the present embodiments include solubility reagents such as, for example, a small amount of an organic solvent such as, e.g., methanol, ethanol, isopropanol, methoxy propanol and DMSO; and agents for carrying out protein digestion such as, for example, proteinases, trypsin, pepsin, peptidases; for example.

The concentration of the releasing agent(s) in the medium is that sufficient to achieve the desired result of displacing the analyte from endogenous binding moieties to render the analyte and, in some instances analyte metabolites, accessible for binding to an antibody for the analyte as discussed above. The amount or concentration of the releasing agent employed depends on one or more of the nature of the sample, the nature of the analyte, the nature of the drug metabolites, the nature of other reagent components, and the reaction conditions, for example. In some embodiments the amount of the releasing agent in the aqueous medium is about 0.000001% to about 0.5%, about 0.0001% to about 0.4%, about 0.001% to about 0.3%, about 0.01% to about 0.2%, about 0.1% to about 0.3%, about 0.2% to about 0.5%, about 0.1% to about 0.2%, for example (percent is weight/volume).

For some analytes such as, for example, immunosuppressant drugs, a lysing agent such as, for example a detergent, may be employed. The detergent makes the immunosuppressant drug more water miscible in an aqueous assay mixture, thus rendering it more accessible by the assay measuring agents such as assay antibodies. In some examples, a detergent is employed that can prevent the drug from diffusing into lipoproteins particles or other type of liposomes. For example, PLURONIC® detergent is a detergent used in a tacrolimus assay to prevent the drug from diffusing into the core of lipoprotein complexes.

One or more incubation periods may be employed in the methods in accordance with the principles described herein. An incubation period may be applied to a medium at one or more intervals including any intervals between additions of various reagents mentioned above. The medium is usually incubated at a temperature and for a time sufficient for the function that is being carried out such as, for example, treatment with a releasing agent, treatment with a pretreatment agent, binding of various components of the reagents such as, for example, binding of antibody to an analyte, to occur. Moderate temperatures are normally employed for carrying out an incubation period. The method may include an incubation period for one or more of the steps of the present methods. For example, an incubation period may be applied to one or more of the combination of the releasing agent with the sample, the combination of the pretreatment agent with the sample and an antibody reagent, the combination of the pretreatment agent with the sample, an antibody reagent and a solid phase reagent, for example. In some examples, the medium is incubated under conditions for binding of the antibody for the analyte to analyte suspected of being in the sample as discussed more fully below.

The length and conditions of the incubation periods are dependent on one or more of the nature and concentration of the reagents, the nature of the analyte, and the suspected concentration of the analyte, for example. In some embodiments incubation temperatures may be about 5° C. to about 99° C., or about 15° C. to about 70° C., or about 20° C. to about 45° C., for example. The time for an incubation period depends on one or more of the temperature of the medium and the rate of reaction or of binding of the various reagents. The time period for the incubation is about 0.2 seconds to about 24 hours, or about 1 second to about 6 hours, or about 2 seconds to about 1 hour, or about 1 to about 15 minutes, for example.

Following an incubation period, if any, for binding of antibody for the analyte to the analyte, the medium is examined for the presence of a complex comprising the analyte and the antibody for the analyte. The presence and/or amount of the complex indicate the presence and/or amount of the analyte in the sample. The phrase "complex comprising the antibody for the analyte" refers to a complex wherein the antibody for the analyte is bound to one or more substances that may be one or more of the analyte and other substances in a sample that bind to the antibody for the analyte.

In many embodiments the examination of the medium involves detection of a signal from the medium. The presence and/or amount of the signal are related to the presence and/or amount of the analyte in the sample. The particular mode of detection depends on the nature of the sps. As discussed above, there are numerous methods by which a label of an sps can produce a signal detectable by external means, desirably by visual examination, and include, for example, electromagnetic radiation, electrochemistry, heat, radioactivity detection, and chemical reagents.

The examination for presence and/or amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, photographic instrument, and the like. The presence and amount of signal detected is related to the presence and amount of the analyte present in a sample if the assay is making an accurate determination. Temperatures during measurements generally range from about 10° to about 70° C. or from about 20° to about 45° C., or about 20° to about 25° C., for example. In one approach standard curves are formed using known concentrations of the analytes to be screened. As discussed herein, calibrators and other controls may also be used.

The phrase "measuring the amount of an analyte" refers to the quantitative, semi-quantitative and qualitative determination of the analyte. Methods that are quantitative, semiquantitative and qualitative, as well as all other methods for determining the analyte, are considered to be methods of measuring the amount of the analyte. For example, a method, which merely detects the presence or absence of the analyte in a sample suspected of containing the analyte, is considered to be included within the scope of the above phrase. The terms "detecting" and "determining," as well as other common synonyms for measuring, are contemplated within the scope of the present disclosure.

General Description of Non-Agglutination Assays for an Analyte

Any suitable non-agglutination assay may be employed for determining an analyte in accordance with the principles described herein. The assay may be conducted on the sample as an immediate continuation of the pretreatment as discussed above or the assay may be carried out at a point thereafter. Thus, a particular assay may be conducted sequentially or concomitantly. The assays are conducted by combining the respective sample with reagents for determining the amount of the analyte in the sample. The nature of the reagents is dependent on the particular type of assay to be performed. In general, the assay is a method for the determination of the amount of an analyte in a sample. Various assay methods are discussed below by way of illustration and not limitation.

The assay comprises adding reagents for determining the concentration of the analyte in the sample to a medium comprising the sample. For immunoassays, the reagents comprise at least one antibody for the analyte or similar sbp member. An amount of a complex comprising the antibody for the analyte is measured and the amount of the complex is related to the concentration of the analyte and other substances in the sample.

One general group of non-agglutination immunoassays that may be employed includes non-agglutination immunoassays using a limited concentration of antibody. Another group of non-agglutination immunoassays involves the use of an excess of one or more of the principal reagents such as, for example, an excess of an antibody for the analyte. Another group of non-agglutination immunoassays are separation-free homogeneous assays in which the labeled reagents modulate the label signal upon analyte-antibody binding reactions. Another group of non-agglutination immunoassays includes labeled antibody reagent limited competitive assays for analyte that avoid the use of problematic labeled haptens. In this type of assay, a solid phase immobilized analyte is present in a constant, limited amount. The partition of a label between the immobilized analyte and free analyte depends on the concentration of analyte in the sample.

Antibodies specific for an analyte for use in immunoassays can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

As discussed above, an antibody selected for use in an immunoassay for an analyte, for example, should specifically and preferentially bind the analyte (and its pharmaceutically active metabolites, if necessary or desired) over other ligands such as other metabolites or related substances. Other reagents are included in the assay medium depending on the nature of the assay to be conducted.

As discussed above, non-agglutination immunoassays may involve labeled reagents. Non-agglutination labeled immunoassays include, but are not limited to, enzyme immunoassays, fluorescence polarization immunoassays, radioimmunoassay, inhibition assay, induced luminescence, and fluorescent oxygen channeling assay, for example.

In some embodiments homogeneous non-agglutination immunoassays may be employed; such assays may also be referred to as essentially partition-free immunoassays. The present methods have application to fully automated homogeneous assays in which, prior to the assay, there is no extraction or separation of the analyte from other constituents of the sample including analyte metabolites. In a "non-manual extraction" assay, a sample such as a whole blood sample, without extraction in, e.g., an organic solvent, is combined with reagents for conducting an assay for the analyte in a suitable medium and the assay method is conducted. The present methods also find application to manual extraction assays.

The assays can be performed either without separation (homogeneous) or with separation (heterogeneous) of any of the assay components or products. Homogeneous immunoassays are exemplified by the EMIT® assay (Syva Company, San Jose, Calif.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and so forth.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), particle enhanced turbidimetric immunoassay ("PETIA"), etc.; and the like.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); acridinium ester label immunoassays using paramagnetic particles as a solid phase (ADVIA Centaur immunoassays); and so forth. Other types of assays include immunosensor assays involving the monitoring of the changes in the optical, acoustic and electrical properties of an antibody-immobilized surface upon the binding of an analyte. Such assays include, for example, optical immunosensor assays, acoustic immunosensor assays, semiconductor immunosensor assays, electrochemical transducer immunosensor assays, potentiometric immunosensor assays, and amperometric electrode assays, for example.

In certain embodiments a second enzyme may be employed in addition to the enzyme of the enzyme conjugate. The enzymes of the pair of enzymes are related in that a product of the first enzyme serves as a substrate for the second enzyme.

In one embodiment the assay is an induced luminescence immunoassay, which is described in U.S. Pat. No. 5,340,716 (Ullman, et al.), which disclosure is incorporated herein by reference. In one approach the assay uses a particle incorporating a photosensitizer and a label particle incorporating a chemiluminescent compound. The label particle is conjugated to an sbp member, for example, an antibody for the analyte that is capable of binding to the analyte to form a complex, or to a second sbp member to form a complex, in relation to the amount of the analyte. If the analyte is present, the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed, which comprises antibody for the analyte.

By way of further illustration, chemiluminescent particles are employed, which comprise the chemiluminescent compound associated therewith such as by incorporation therein or attachment thereto. An sbp member that binds to the analyte, such as, for example, an antibody for analyte, is bound to a polysaccharide coating the particles. A second sbp member that binds to the analyte is part of a biotin conjugate. Streptavidin is conjugated to a second set of particles having a photosensitizer associated therewith. The binding of the streptavidin to this second set of particles (photosensitizer particles) may or may not involve a polysaccharide on the particles. The chemiluminescent particles are mixed with the respective portion of the sample suspected of containing an analyte and with the photosensitizer particles. The reaction medium is incubated to allow the particles to bind to the analyte by virtue of the binding of the sbp members to the analyte. Then, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of the substances and/or the analyte, it is activated by singlet oxygen and emits luminescence. The medium is then examined for the amount of luminescence or light emitted, the presence thereof being related to the amount of the substances that bind to antibody for the analyte or the amount of analyte.

Another particular example of an assay that may be employed for the determination of an analyte is discussed in U.S. Pat. No. 5,616,719 (Davalian, et al.), which describes fluorescent oxygen channeling immunoassays.

Another embodiment of an assay format is a capture assay. In this assay format, the antibody for the analyte is covalently bound to a magnetic particle. The sample is incubated with these particles to allow the antibodies for the analyte to bind to the analyte and/or substances in the sample other than analyte that also bind to the antibody. Subsequently, an enzyme that has the analyte or a derivative of the analyte covalently attached is incubated with the magnetic particles. After washing, the amount of enzyme that is bound to the magnetic particles is measured and is inversely related to the amount of a complex comprising the antibody for the analyte. Alternatively, the amount of enzyme in the supernatant liquid is measured and is directly related to the amount of a complex comprising the antibody for the analyte.

The assays discussed above are normally carried out in an aqueous buffered medium at a moderate pH, generally that which provides optimum assay sensitivity and does not interfere with the assay employed. The pH for the assay medium will usually be in the range of about 4 to about 11, or in the range of about 5 to about 10, or in the range of about 6.5 to about 9.5. The pH will usually be a compromise between optimum binding of the binding members of any specific binding pairs, the pH optimum for other reagents of the assay such as members of a signal producing system, and so forth.

Various buffers may be used to achieve the desired pH and maintain the pH during the determination. Illustrative buffers include borate, phosphate, carbonate, tris, barbital and the like. The particular buffer employed is not critical, but in an individual assay one or another buffer may be preferred. Various ancillary materials may be employed in the above methods. For example, in addition to buffers the medium may comprise stabilizers for the medium and for the reagents employed. In some embodiments, in addition to these additives, proteins may be included, such as albumins; quaternary ammonium salts; polyanions such as dextran sulfate; binding enhancers, or the like. All of the above materials are present in a concentration or amount sufficient to achieve the desired effect or function.

As mentioned above, one or more incubation periods may be applied to the medium at one or more intervals including any intervals between additions of various reagents mentioned above. Conditions for an incubation period are discussed above.

The concentration of analyte that may be assayed generally varies from about $10^{-5}$ to about $10^{-17}$ M, or from about $10^{-6}$ to about $10^{-14}$ M. Considerations, such as whether the assay is qualitative, semi-quantitative or quantitative (relative to the amount of analyte present in the sample), the particular detection technique and the concentration of the analyte normally determine the concentrations of the various reagents.

The concentrations of the various reagents in the assay medium will generally be determined by the concentration range of interest of the analyte, the nature of the assay, the antibody affinity and avidity and antibody fragmentation, for example. However, the final concentration of each of the reagents is normally determined empirically to optimize the sensitivity of the assay over the range. That is, a variation in concentration of analyte that is of significance should provide an accurately measurable signal difference. Considerations such as the nature of a signal producing system and the nature of the analyte normally determine the concentrations of the various reagents.

While the order of addition may be varied widely, there will be certain preferences depending on the nature of the non-agglutination assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition as discussed above.

Specific Examples of Non-Agglutination Immunoassays for Determination of an Immunosuppressant Drug The following specific examples are by way of illustration and not limitation on the scope of the present disclosure. Selection of tacrolimus or sirolimus as the immunosuppressant drug is also by way of illustration and not limitation as the present disclosure has general application to detection of analytes in general and immunosuppressant drugs in particular.

The sample to be analyzed is one that is suspected of containing one or more immunosuppressant drug analytes. In these examples, the sample is whole blood, which is unfractionated blood or blood that comprises both red cells and plasma. The sample is treated with one or more releasing agents to release immunosuppressant drug analyte from endogenous-binding substances. For the immunosuppressant drug in this example, the releasing agents may include one or more of a lysing agent and a hemolytic agent as discussed above to release the immunosuppressant drug from red blood cells. The nature and amount or concentration of hemolytic agent and/or lysing agent employed is discussed above. The sample and an antibody reagent are also subjected to a pretreatment agent as described above, which may be carried out as a separate step, or the pretreatment agent may be included in the medium with one or more releasing agents. Thus, all of the above may be combined simultaneously in the medium or one or more of the above reagents may be added sequentially in concentrations as discussed above. The medium may also comprise one or more preservatives as are known in the art.

In one example, following treatment with one or more releasing agents that include FK506 ester, a sample suspected of containing tacrolimus in an assay medium is mixed with a tacrolimus conjugate, i.e., for example, an analog of tacrolimus that is attached to biotin. The sample is incubated to allow binding of tacrolimus of the sample to the antibody for tacrolimus in competition with the analog of tacrolimus where the antibody is capable of binding to tacrolimus or the analog of tacrolimus. The medium also includes sodium salicylate as a pretreatment agent as discussed above. After rinsing with an appropriate wash buffer, a detection molecule consisting of streptavidin or avidin conjugated to an enzyme, florescent or chemiluminescent molecule or radioactive moiety can be added to the medium, which is then examined for the amount of signal. The amount of signal is related to the amount of tacrolimus in the sample.

In another example, a non-agglutination immunoassay employed is an induced luminescence assay as described above. In some embodiments of the induced luminescence assay by way of illustration and not limitation, the reagents include two latex bead reagents and a biotinylated anti-tacrolimus mouse monoclonal antibody. The first bead reagent is coated with tacrolimus or a tacrolimus analog and contains chemiluminescent dye. The second bead reagent is coated with streptavidin and contains a photosensitizer dye. A medium containing a sample suspected of containing tacrolimus and an antibody reagent is treated with trichloroacetic acid as a pretreatment agent as discussed above, where the medium can contain one or more releasing agents that include FK506 to release tacrolimus from endogenous binding substances in the sample. After conducting the assay, the resulting chemiluminescent signal is measured at 612 nm and is an inverse function of the concentration of tacrolimus in the sample that binds to tacrolimus antibody.

Another specific example in accordance with the principles described herein involves an assay format known as ACMIA (Affinity Chromium dioxide Mediated Immuno Assay). For the ACMIA assay format, chrome particles, which are coated with sirolimus or a sirolimus analog, are employed as a first component. A second component is an antibody for sirolimus. This antibody, crosslinked to a reporter enzyme (for example, beta-galactosidase), is added to a reaction vessel in an excess amount, i.e., an amount greater than that required to bind all of the analyte that might be present in a sample. Following treatment with sodium salicylate as a pretreatment agent as discussed above and with one or more releasing agents that include tacrolimus ester, the medium comprising the sample suspected of containing sirolimus and the antibody-enzyme conjugate is incubated to allow the sirolimus analyte to bind to the antibody. Next, the chrome particle reagent is added to bind up any excess antibody-enzyme conjugate. Then, a magnet is applied, which pulls all of the chrome particles and excess antibody-enzyme out of the suspension, and the supernatant is transferred to a final reaction container. The substrate of the reporter enzyme is added to the final reaction container, and the enzyme activity is measured spectrophotometrically as a change in absorbance over time. The amount of this signal is related to the amount of sirolimus in the sample.

In a sandwich assay format, by way of example, a first reagent comprising chrome particles coated with anti-tacrolimus antibodies and a second reagent comprising a second antibody (or binding protein) for the first antibody conjugated to a reporter enzyme are employed. Following treatment with sodium salicylate as a pretreatment agent as discussed above and with one or more releasing agents that include FK506, a sample suspected of containing tacrolimus and the chrome particles is incubated so that all of the tacrolimus, if present in the sample, becomes bound to the chrome particles. The chrome particles are washed, using a magnet to separate the bound analyte from the supernatant. Then, the second reagent, i.e., antibody (or binding protein) conjugated to a reporter enzyme, is incubated with the chrome particles to form a "sandwich". After washing, the amount of enzyme that is bound to the chrome is measured and is related to the amount of tacrolimus in the sample.

Another specific example of an assay format, for purposes of illustration and not limitation, is EMIT® (Enzyme-Mediated Immunoassay Technology). Following treatment with trichloroacetic acid as a pretreatment agent as discussed above and with one or more releasing agents that include tacrolimus ester, a medium comprising the sample suspected of containing sirolimus and an antibody for sirolimus, an enzyme conjugate, for example, a conjugate of G-6-PDH, is incubated for an appropriate time period. After conducting the assay, the amount of enzyme activity is measured and is related to the amount of sirolimus in the sample.

Kits for Conducting Non-Agglutination Immunoassays

The reagents for conducting a particular assay may be present in a kit useful for conveniently performing an assay for the determination of an analyte. In one embodiment a kit comprises in packaged combination a pretreatment agent in accordance with the principles described herein, reagents for releasing an analyte from endogenous binding substances, an antibody for an analyte and other reagents for performing a non-agglutination immunoassay, the nature of which depend upon the particular assay format. The reagents may each be in separate containers or various reagents can be combined in one or more containers depending on the cross-reactivity and stability of the reagents. The kit can further include other separately packaged reagents for conducting an assay such as additional sbp members, ancillary reagents such as an ancillary enzyme substrate, and so forth.

The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay. The kit can further include a written description of a method in accordance with the present embodiments as described above.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The following examples further describe the specific embodiments of the present disclosure by way of illustration and not limitation and are intended to describe and not to limit the scope of the inventive concept(s). Parts and percentages disclosed herein are by volume unless otherwise indicated.

EXAMPLES

All chemicals may be purchased from the Sigma-Aldrich Company (St. Louis Mo.) unless otherwise noted. Tacrolimus may be obtained from Astellas Pharma US. Inc., Deerfield Ill.

Testing is carried out using the DIMENSION® RxL analyzer, available from Siemens Healthcare Diagnostics Inc., Newark Del. The instrument is employed using ACMIA immunoassay technology. The ACMIA assay method is described in U.S. Pat. Nos. 7,186,518, 5,147,529, 5,128,103, 5,158,871, 4,661,408, 5,151,348, 5,302,532, 5,422,284, 5,447,870, and 5,434,051, the disclosures of which are incorporated herein in their entirety. In the embodiment of the ACMIA method used herein and discussed in more detail below, competition between tacrolimus analog on chrome particles and tacrolimus in patient samples for antibody for tacrolimus conjugated to an enzyme (the "conjugate") is utilized to determine the amount of tacrolimus in patient samples. Conjugate that binds to the tacrolimus analog on chrome particles is removed by magnetic separation. The enzymatic activity from conjugate remaining in the supernatant is measured and is directly proportional to the amount of tacrolimus in the patient sample. In the ACMIA assay format employed, the enzymatic activity observed when testing a sample containing no tacrolimus is indicative of the amount of enzymatic activity that is not bound to active antibody (i.e., cannot bind tacrolimus on chrome particles). The enzymatic activity observed when no chrome particle is present is indicative of the total amount of enzymatic activity in the conjugate. These values can be used to estimate the percent of enzymatic activity bound to active antibody.

The following terms used herein are defined as follows: "µg" is microgram(s); "mL" is milliliter(s); "mg" is milligram(s); "µL" is microliter(s); and "ng" is nanogram(s)

Example 1: Automated Non-Agglutination Immunoassay for Tacrolimus

Preparation of Pretreatment Solution.

This pretreatment solution contained sirolimus, sodium azide, Pipes 1.5 sodium salt, EDTA disodium dehydrate, saponin, PLURONIC® 25R2, PROCLIN® 300, neomycin sulfate and pretreatment agent (sodium trichloroacetate, sodium salicylate or a combination of both.

Preparation of Anti-Tacrolimus Antibody-β-Galactosidase Conjugate.

Monoclonal anti-tacrolimus antibody (clone 1H6 from Siemens Healthcare Diagnostics Inc, Glasgow, Del.) is conjugated to β-galactosidase using a standard heterobifunctional SMCC (succinimidyl trans-4-(N-maleimidylmethyl) cyclohexane-1-carboxylate) linker according to known techniques. The antibody conjugate solution contains approximately 7.5 µg/mL anti-tacrolimus antibody-β-galactosidase conjugate, 30 mg/mL protease free bovine serum albumin, 0.126 mg/mL $MgCl_2$, 0.03 mL/mL of ethylene glycol, 35.14 mg/mL PIPES 1.5 sodium salt, 50 mg/mL NaCl and beta-gal mutein (inactivated beta-galactosidase), pH 6.5.

Magnetic Chrome Particle Preparation.

Tacrolimus chrome particles (immunoassay solid phase) are prepared by conjugating tacrolimus-C22 to fluorescein, which is used to pre-decorate anti-fluorescein antibody immobilized on chromium dioxide particles through glutaraldehyde. The chrome particle reagent contains approximately 2.5 mg/mL tacrolimus chrome particle slurry, 60.8 mg/mL trehalose dihydrate and 7.2 mg/mL CARBOWAX®.

Non-agglutination Assay for Tacrolimus. The principle and operation of the ACMIA assay for tacrolimus employing a pretreatment agent in accordance with the principles described herein is as follows: 15 µL of a whole blood sample suspected of containing tacrolimus is mixed with the hemolytic pretreatment solution in a vessel on the DIMENSION® RxL analyzer. The whole blood is sampled from a standard cup by first mixing the blood with the ultrasonic sample probe. The mixing of whole blood sample with the pretreatment solution ensures the hemolysis of the whole blood and the displacement of the protein-bound tacrolimus molecules from their binding sites when the sirolimus molecules were present.

Anti-tacrolimus antibody-β-galactosidase conjugate (50 µL) is added next to each of the reaction vessels and the mixture is held for a period of time (10 to 15 minutes) and at a temperature of 43° C. to allow tacrolimus, if present, to react with the antibody reagent. Chrome particles with immobilized tacrolimus-CMO-DA10-Dexal prepared as described above are added (50 µL) to each of the reaction vessels and are allowed to bind un-bound conjugate. The tacrolimus-bound anti-tacrolimus antibody-β-galactosidase conjugate does not bind to the chrome particles but remains in the supernatant when a magnetic field is applied to the above reaction mixtures to separate the solution from the chrome particles. The tacrolimus-bound conjugate is detected by transferring the supernatant from each of the reaction vessels to a photometric cuvette and measuring the enzymatic rate of the conjugate in the presence of chlorophenol red-β-D-galactopyranoside (CPRG). The rate for each reaction vessel is measured bichromatically at 577 and 700 nm.

For purposes of comparison, the pretreatment solution above was employed without a pretreatment agent in accordance with the principles described herein.

Sodium Trichloroacetate as Pretreatment Agent.

Table 1 shows the composition of the pretreatment solution, which contains a pretreatment agent in accordance with the principles described herein. Qty is quantity. EDTA is ethylenediaminetetraacetate.

TABLE 1

| Pretreatment Solution | |
| --- | --- |
| Name | Qty (mg/mL) |
| Sirolimus | 0.0012 |
| Sodium Trichloroacetate | 135 |
| Sodium Azide | 0.99 |
| Pipes 1.5 Sodium salt | 6.8 |
| EDTA disodium dihydrate | 0.3 |
| Saponin | 1 |
| PLURONIC ® 25R2 | 0.9 |
| PROCLIN ® 300 | 0.4 |
| Neomycin sulfate | 0.024 |

Table 2 shows the comparison between the pretreatment solution containing a pretreatment agent (12% sodium trichloroacetate) in accordance with the principles described herein and the pretreatment solution that does not contain a pretreatment agent. In the following tables, LC/MS$^2$ is liquid chromatography/mass spectrometry performed on a tandem mass spectrometer using a reverse phase column. TCA is sodium trichloroacetate (pretreatment agent). PT is pretreatment solution. Control represents the use of a pretreatment reagent that does not contain TCA.

TABLE 2

| LC/MS$^2$ ng/mL | 12% TCA in PT (ng/mL) | Control No TCA in PT (ng/mL) |
| --- | --- | --- |
| 11.8 | 11.9 | 10.2 |
| 5.7 | 5.7 | 4.2 |
| 2.9 | 2.8 | 2.2 |
| 0.1 | −0.3 | −0.1 |
| 5.9 | 5.9 | 5.1 |
| 6.8 | 6.7 | 5.1 |
| 4.8 | 4.8 | 3.9 |
| 10.5 | 10.8 | 9.8 |
| 15.1 | 15.6 | 13.9 |
| 6.8 | 7.4 | 5.9 |
| 7.6 | 7.7 | 6.3 |
| 8.2 | 8.2 | 6.9 |
| 6.6 | 6.7 | 5.6 |
| 4.1 | 3.8 | 3.1 |
| 12.3 | 11.7 | 10.6 |
| 4.1 | 4.1 | 3.3 |
| 5.9 | 6.0 | 5.3 |
| 4.8 | 4.8 | 4.3 |

As can be seen from the results in Table 2, the use of a pretreatment agent in accordance with the principles described herein obtains assay results that closely parallel those obtained using LC/MS$^2$ whereas the Control does not.

Sodium Salicylate as Pretreatment Agent.

Table 3 shows the composition of the pretreatment solution, which contains a pretreatment agent (5% sodium salicylate) in accordance with the principles described herein.

TABLE 3

| Pretreatment Solution | |
| --- | --- |
| Name | Qty (mg/mL) |
| Sirolimus | 0.0012 |
| Sodium Salicylate | 50 |
| Sodium Azide | 0.99 |
| Pipes 1.5 Sodium salt | 6.8 |
| EDTA disodium dihydrate | 0.3 |
| Saponin | 1 |
| PLURONIC ® 25R2 | 0.9 |
| PROCLIN ® 300 | 0.4 |
| Neomycin sulfate | 0.024 |

Table 4 shows the comparison between the pretreatment solution containing a pretreatment agent (5% sodium salicylate) in accordance with the principles described herein and the pretreatment solution that does not contain a pretreatment agent.

TABLE 4

| LC/MS$^2$ | 5% Salicylate in PT (ng/ML) | Control No Salicylate in PT (ng/mL) |
| --- | --- | --- |
| 3.1 | 3.4 | 4.6 |
| 5.1 | 4.7 | 3.8 |

As can be seen from the results in Table 4, the use of a pretreatment agent in accordance with the principles described herein obtains assay results that closely parallel those obtained using LC/MS whereas the Control does not.

Combination of Sodium Salicylate and Sodium Trichloroacetate as Pretreatment Agent.

Table 5 shows the composition of the pretreatment solution, which contains a pretreatment agent (1% sodium salicylate/11% sodium trichloroacetate) in accordance with the principles described herein.

TABLE 5

Pretreatment Solution

| Name | Qty (mg/mL) |
|---|---|
| Sirolimus | 0.0012 |
| Sodium Salicylate | 10 |
| Sodium Trichloroacetate | 110 |
| Sodium Azide | 0.99 |
| Pipes 1.5 Sodium salt | 6.8 |
| EDTA disodium dihydrate | 0.3 |
| Saponin | 1 |
| PLURONIC ® 25R2 | 0.9 |
| PROCLIN ® 300 | 0.4 |
| Neomycin sulfate | 0.024 |

Table 6 shows the comparison between the pretreatment solution containing a pretreatment agent (1% sodium salicylate/11% sodium trichloroacetate) in accordance with the principles described herein and the pretreatment solution that does not contain a pretreatment agent.

TABLE 6

| LC/MS$^2$ | 1% Salicylate/ 11% TCA in PT (ng/mL) | Control No Salicylate/TCA (ng/mL) |
|---|---|---|
| 3.1 | 3.2 | 4.6 |
| 5.1 | 4.7 | 3.8 |

As can be seen from the results in Table 6, the use of a pretreatment agent in accordance with the principles described herein obtains assay results that closely parallel those obtained using LC/MS whereas the Control does not.

All publications and patent applications cited in this specification are herein incorporated by reference as if each individual publication or patent application were specifically and individually indicated to be incorporated by reference.

Although the foregoing inventive concept(s) has been described in some detail by way of illustration and example for purposes of clarity of understanding, it will be readily apparent to those of ordinary skill in the art in light of the teachings of the present disclosure that certain changes and modifications may be made thereto without departing from the spirit or scope of the appended claims. Furthermore, the foregoing description, for purposes of explanation, used specific nomenclature to provide a thorough understanding of the inventive concept(s). However, it will be apparent to one skilled in the art that the specific details are not required in order to practice the inventive concept(s). Thus, the foregoing descriptions of specific embodiments of the present disclosure are presented for purposes of illustration and description; they are not intended to be exhaustive or to limit the inventive concept(s) to the precise forms disclosed. Many modifications and variations are possible in view of the above teachings. The embodiments were chosen and described in order to explain the principles of the inventive concept(s) and its practical applications and to thereby enable others skilled in the art to utilize the inventive concept(s).

What is claimed is:

1. A method of determining an amount of an immunosuppressant drug present in a biological sample suspected of containing the immunosuppressant drug while minimizing inaccuracies resulting from interfering substances present in the biological sample, wherein the immunosuppressant drug is sirolimus, the method comprising a non-agglutination immunoassay comprising:
    (a) providing in combination in an aqueous medium:
        (i) the biological sample, wherein the biological sample has not been exposed to an extraction or separation step to extract or separate the analyte from other constituents of the biological sample;
        (ii) a releasing agent for releasing sirolimus from endogenous binding substances, wherein the releasing agent is a structural analog of sirolimus;
        (iii) a pretreatment agent selected from the group consisting of hydroxyphenyl-substituted C1-C5 carboxylic acids and metallic salts thereof and halogen-substituted C1-C5 carboxylic acids and metallic salts thereof in an amount effective to enhance the accuracy of the non-agglutination immunoassay by minimizing false results in an assay measurement caused by non-specific binding, wherein the pretreatment agent is present in the aqueous medium at a concentration in a range of from about 1% to about 3%;
    (b) incubating the medium under conditions that allow for release of sirolimus from endogenous binding proteins present in the biological sample;
    (c) adding to the incubated medium, either simultaneously or wholly or partially sequentially, competitive assay components (iv) and (v):
        (iv) a competitive sirolimus reagent, wherein the competitive sirolimus reagent comprises sirolimus or an analog thereof; and
        (v) an antibody reagent comprising an antibody for sirolimus, wherein the antibody specifically binds to the competitive sirolimus reagent but does not specifically bind to the structural analog of sirolimus present in the releasing agent; and
        wherein one of (iv) and (v) is immobilized and the other of (iv) and (v) is labeled;
    (d) incubating the medium under conditions that allow for binding of the antibody to sirolimus present in the biological sample or to the competitive sirolimus reagent, wherein the incubation temperature is 5° C. to 99° C. and the time period for the incubation is in a range of from about 0.2 seconds to about 24 hours;
    (e) determining an amount of a complex formed of (iv) and (v) present in the medium, wherein the amount of sirolimus present in the biological sample is inversely proportional to the amount of complex present.

2. The method of claim 1, wherein the structural analog of sirolimus in (ii) is selected from the group consisting of everolimus, a sirolimus ester, tacrolimus, and a tacrolimus ester.

3. The method of claim 1, wherein the releasing agent is present in the aqueous medium in step (a) at a concentration in a range of from about 0.000001% to about 0.5%.

4. The method according to claim 1, wherein the pretreatment agent is a metallic salt of salicylic acid, a metallic salt of a chloro-substituted C1-C5 carboxylic acid, a metallic salt of a chloro-substituted acetic acid, or a metallic salt of trichloroacetic acid.

5. The method according to claim 1, wherein (iv) comprises an enzyme label, and (v) is immobilized on a magnetic particle.

6. The method according to claim 1, wherein the releasing agent further comprises a solubility agent.

7. The method according to claim 6, wherein the solubility agent comprises DMSO.

8. The method according to claim 1, wherein the non-agglutination immunoassay is selected from the group consisting of an enzyme immunoassay, a radioimmunoassay, an inhibition assay, an induced luminescence, a fluorescent oxygen channeling assay, and a fluorescence polarization assay.

9. A method of determining an amount of an immunosuppressant drug present in a biological sample suspected of containing the immunosuppressant drug while minimizing inaccuracies resulting from interfering substances present in the biological sample, wherein the immunosuppressant drug is tacrolimus, the method comprising a non-agglutination immunoassay comprising:
  (a) combining, either simultaneously or wholly or partially sequentially, in an aqueous medium:
    (i) the biological sample, wherein the biological sample has not been exposed to an extraction or separation step to extract or separate the analyte from other constituents of the biological sample;
    (ii) a releasing agent for releasing tacrolimus from endogenous binding substances, wherein the releasing agent is a structural analog of tacrolimus;
    (iii) a pretreatment agent selected from the group consisting of hydroxyphenyl-substituted C1-C5 carboxylic acids and metallic salts thereof and halogen-substituted C1-C5 carboxylic acids and metallic salts thereof in an amount effective to enhance the accuracy of the non-agglutination immunoassay by minimizing false results in an assay measurement caused by non-specific binding, wherein the pretreatment agent is present in the aqueous medium at a concentration in a range of from about 1% to about 3%;
  (b) incubating the medium under conditions that allow for release of tacrolimus from endogenous binding proteins present in the biological sample;
  (c) adding to the incubated medium, either simultaneously or wholly or partially sequentially, competitive assay components (iv) and (v):
    (iv) a competitive tacrolimus reagent, wherein the competitive tacrolimus reagent comprises tacrolimus or an analog thereof; and
    (v) an antibody reagent comprising an antibody for tacrolimus, wherein the antibody specifically binds to the competitive tacrolimus reagent but does not specifically bind to the structural analog of tacrolimus present in the releasing agent; and
    wherein one of (iv) and (v) is immobilized and the other of (iv) and (v) is labeled;
  (d) incubating the medium under conditions that allow for binding of the antibody to tacrolimus present in the biological sample or to the competitive tacrolimus reagent, wherein the incubation temperature is 5° C. to 99° C. and the time period for the incubation is in a range of from about 0.2 seconds to about 24 hours;
  (e) determining an amount of a complex formed of (iv) and (v) present in the medium, wherein the amount of tacrolimus present in the biological sample is inversely proportional to the amount of complex present.

10. The method of claim 9, wherein the structural analog of tacrolimus of (ii) is selected from the group consisting of sirolimus, a sirolimus ester, and a tacrolimus ester.

11. The method of claim 9, wherein the releasing agent is present in the aqueous medium in step (a) at a concentration in a range of from about 0.000001% to about 0.5%.

12. The method according to claim 9, wherein the pretreatment agent is a metallic salt of salicylic acid, a metallic salt of a chloro-substituted C1-C5 carboxylic acid, a metallic salt of a chloro-substituted acetic acid, or a metallic salt of trichloroacetic acid.

13. The method according to claim 9, wherein (iv) comprises an enzyme label, and (v) is immobilized on a magnetic particle.

14. The method according to claim 9, wherein the releasing agent further comprises a solubility agent.

15. The method according to claim 14, wherein the solubility agent comprises DMSO.

16. The method according to claim 9, wherein the non-agglutination immunoassay is selected from the group consisting of an enzyme immunoassay, a radioimmunoassay, an inhibition assay, an induced luminescence, a fluorescent oxygen channeling assay, and a fluorescence polarization assay.

* * * * *